(12) United States Patent
Srivastava et al.

(10) Patent No.: US 9,637,503 B2
(45) Date of Patent: May 2, 2017

(54) COMPOSITION OF MATTER

(71) Applicant: University of Louisiana at Lafayette, Lafayette, LA (US)

(72) Inventors: Radhey S. Srivastava, Youngsville, LA (US); Siva Murru, Lafayette, LA (US)

(73) Assignee: University of Louisiana at Lafayette, Lafayette, LA (US)

( * ) Notice: Subject to any disclaimer, the term of this patent is extended or adjusted under 35 U.S.C. 154(b) by 0 days.

(21) Appl. No.: 15/186,823

(22) Filed: Jun. 20, 2016

(65) Prior Publication Data
US 2016/0304538 A1    Oct. 20, 2016

Related U.S. Application Data

(63) Continuation-in-part of application No. 14/418,540, filed as application No. PCT/US2013/054011 on Aug. 7, 2013, now Pat. No. 9,394,229.

(60) Provisional application No. 61/680,551, filed on Aug. 7, 2012.

(51) Int. Cl.
*C07F 1/08* (2006.01)
*C07F 1/00* (2006.01)

(52) U.S. Cl.
CPC .................................. *C07F 1/005* (2013.01)

(58) Field of Classification Search
CPC ....................................................... C07F 1/005
See application file for complete search history.

(56) References Cited

U.S. PATENT DOCUMENTS

2010/0056806 A1* 3/2010 Warren ................ B01J 31/1805
548/954

OTHER PUBLICATIONS

Srivastava, R. et al. "Mechanistic studies of Copper (I)-catalyzed allylic amination." Journal of the American Chemical Society 129.49 (2007): 15250-15258, Table 1.*
Kalita, B, et al. "Copper-catalyzed allylic hydroxyamination and amination of alkenes with Boxhydroxylamine." Tetrahedron letters 46.9 (2005): 1451-1453.*
Telfer, et al. "1, 1-Binaphthyl-2, 2-diol and 2, 2-diamino-1, -binaphthyl: versatile frameworks for chiral ligands in coordination and metallosupramolecular chemistry." Coordination Chemistry Reviews 242.1 (2003): 33-46.*
Weiner, Barbara, et al. "Recent advances in the catalytic asymmetric synthesis of -amino acids." Chemical Society Reviews 39.5 (2010): 1656-1691.*
Che et al, European Journal of Inorganic Chemistry, 2002, (6), 1456-1463.*
Murru et al, European Journal of Organic Chemistry, 2014, 2014(10), 2174-2181.*

* cited by examiner

*Primary Examiner* — Shailendra Kumar
(74) *Attorney, Agent, or Firm* — Robert Devin Ricci; Russel O. Primeaux; Kean Miller LLP

(57) ABSTRACT

The method relates to the field of asymmetric allylic amination and comprises preparing a chiral N-substituted allylic amine compound from the corresponding allylic substrates and substituted hydroxylamines, in the presence of a catalyst, said catalyst comprising copper compounds and a chiral ligand. Examples of chiral amine compounds which can be made using the method include Vigabatrin, Ezetimibe Terbinafine, Naftifine 3-methylmorphine, Sertraline, Cinacalcet, Mefloquine hydrochloride, and Rivastigmine. There are over 20,000 known bioactive molecules with chiral N-substituted allylic amine substructure. The method may also be used to produce non-natural chiral β-aminoacid esters, a sub-class of chiral N-substituted allylic amine compounds. Examples of β-aminoacid ester which can be produced by the disclosed method, include, but are not limited to, N-(2-methylpent-1-en-3-yl)benzenamine and Ethyl 2-methylene-3-(phenylamino)butanoate. Further, the products of the method described herein can be used to produce chiral heterocycles and bioactive molecules or materials. A novel chiral copper-BINAM nitrosoarene complex is also set forth.

8 Claims, 2 Drawing Sheets

Chiral β-aminoacid esters     Asymmetric Allylic Amination     Chiral amines

COMPOSITION OF MATTER

CROSS REFERENCE TO RELATED APPLICATIONS

This application is a continuation-in-part ("CIP") of U.S. patent application Ser. No. 14/418,540, now U.S. Pat. No. 9,394,229 entitled "METHOD OF PRODUCING CHIRAL N-SUBSTITUTED ALLYLIC AMINE COMPOUNDS", filed on Jan. 30, 2015, which was filed under 35 U.S.C. §371 and claims priority to the PCT Application No. PCT/US2013/054011, filed on Aug. 7, 2013, which claims priority to a provisional application, U.S. Application No. 61/680,551, which was filed on Aug. 7, 2012.

STATEMENT REGARDING FEDERALLY SPONSORED RESEARCH OR DEVELOPMENT

Not Applicable.

REFERENCE TO A "SEQUENCE LISTING," A TABLE, OR A COMPUTER PROGRAM

Not Applicable.

DESCRIPTION OF THE DRAWINGS

The drawings constitute a part of this specification and include exemplary embodiments of the method of producing chiral N-substituted allylic amine compounds. It is to be understood that in some instances, various aspects of the invention may be shown exaggerated or enlarged to facilitate an understanding of the invention. Therefore the drawings may not be to scale. In addition, in the embodiments depicted herein, like reference numerals in the various drawings refer to identical or near identical structural elements.

DETAILED DESCRIPTION

Figure 1:
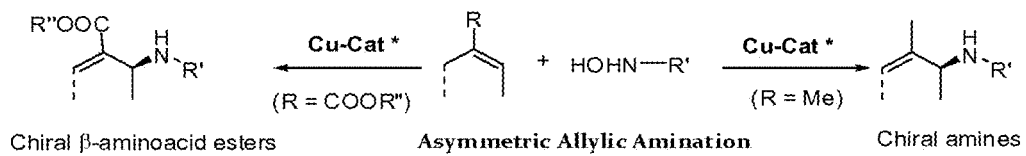
FIG. 1 is a diagram of the method for producing chiral N-substituted allylic amine compounds.

The subject matter herein is described with specificity to meet statutory requirements. However, the description itself is not intended to necessarily limit the scope of claims. Rather, the claimed subject matter might be embodied in other ways to include different steps or combinations of steps similar to the ones described in this document, in conjunction with other present or future technologies.

Many natural products, pharmaceutical compounds, and agrochemicals contain chiral amine functionality. The antiepileptic drug Vigabatrin ((R or S)-4-aminohex-5-enoic acid) and the cholesterol lowering drug Ezetimibe ((3R,4S)-1-(4-fluorophenyl)-3-[(3S)-3-(4-fluorophenyl)-3-hydroxypropyl]-4-(4-hydroxyphenyl)azetidin-2-one) are examples of two commercially useful chiral amine compounds that can be produced by the described method. Terbinafine ([(2E)-6,6-dimethylhept-2-en-4-yn-1-yl](methyl)(naphthalene-1-ylmethyl)amine) and Naftifine ((2E)-N-methyl-N-(1-naphthylmethyl)-3-phenylprop-2-en-1-amine) are examples of two commercially useful N-substituted allylic amine compounds. Examples of commercially useful chiral amine based compounds include 3-methylmorphine ((5α, 6α)-7,8-didehydro-4,5-epoxy-3-methoxy-17-methylmorphinan-6-ol) (pain relief), Sertraline ((1S, 4S)-4-(3,4-dichlorophenyl)-N-methyl-1,2,3,4-tetrahydronaphthalen-1-amine) (depression), Cinacalcet (R)—N-[1-(1-naphthyl)ethyl]-3-[3-(trifluoromethyl)phenyl]propan-1-amine (hyperparathyroidism), Mefloquine hydrochloride ([(R,S)-2,8-bis(trifluoromethyl)quinolin-4-yl]-(2-piperidyl) methanol) (malaria), and Rivastigmine ((S)-3-[1-(dimethylamino)ethyl]phenyl N-ethyl-N-methylcarbamate) (Alzheimers). There are over 20,000 known bioactive molecules with chiral N-substituted allylic amine substructure. Current efforts in asymmetric allylic amination use pre-functionalized allylic substrates and Pd, Rh or Ir-based chiral complexes as catalysts. Additionally, chiral β-aminoacids have been produced using Aza Byalis-Hillman reactions utilizing N-protected imines and α,β-unsaturated carbonyl compounds.

A method for producing chiral N-substituted allylic amine compounds is described herein. The method comprises preparation of a chiral N-substituted allylic amine from the corresponding olefins and hydroxylamines, in the presence of a catalyst. The catalyst comprises a copper compound and a chiral ligand. The aminating agents are substituted hydroxylamines. The method may be used to produce non-natural chiral β-aminoacid esters, a sub-class of chiral N-substituted allylic amines. Further, the products of the method disclosed can be used to produce chiral heterocycles, and bioactive molecules or materials.

The method comprises mixing an olefin compound containing allylic C—H group, with an aminating reagent. The aminating reagent comprises a substituted hydroxylamine. The method further comprises adding a chiral ligand and a copper (Cu(I)) compound to the mixture. The active catalyst is formed in situ by the reaction of the copper [Cu(I)] compound with the chiral ligand. The reaction results in the production of a chiral allyl amine through asymmetric allylic amination. This is a nitroso-ene reaction in which nitroso compounds are generated in situ via oxidation of hydroxylamines by the metal catalyst. The reaction results in very good yields and high enantioselectivity rate.

Through the above described method, a variety of chiral allyl amines may be produced. The antiepileptic drug Vigabatrin ((R or S)-4-aminohex-5-enoic acid) and the cholesterol lowering drug Ezetimibe ((3R,4S)-1-(4-fluorophenyl)-3-[(3S)-3-(4-fluorophenyl)-3-hydroxypropyl]-4-(4-hydroxyphenyl)azetidin-2-one) are two non-limiting examples of two commercially useful chiral amine compounds that can be produced by the described method. Terbinafine ([(2E)-6,6-dimethylhept-2-en-4-yn-1-yl](methyl)(naphthalene-1-ylmethyl)amine) and Naftifine ((2E)-N-methyl-N-(1-naphthylmethyl)-3-phenylprop-2-en-1-amine) are examples of two commercially useful N-substituted allylic amine compounds. Examples of commercially useful chiral amine based compounds include 3-methylmorphine ((5α, 6α)-7,8-didehydro-4,5-epoxy-3-methoxy-17-methylmorphinan-6-ol) (pain relief), Sertraline ((1S, 4S)-4-(3,4-dichlorophenyl)-N-methyl-1,2,3,4-tetrahydronaphthalen-1-amine) (depression), Cinacalcet (R)-N-[1(1-naphthyl)ethyl]-3-[3-(trifluoromethyl)phenyl]propan-1-amine (hyperparathyroidism), Mefloquine hydrochloride ([(R,S)-2,8-bis(trifluoromethyl)quinolin-4-yl]-(2-piperidyl) methanol) (malaria), and Rivastigmine ((S)-3-[1-(dimethylamino)ethyl]phenyl N-ethyl-N-methylcarbamate) (Alzheimers). There are over 20,000 known bioactive molecules with chiral N-substituted allylic amine substructure. Additionally, the method may be used in the production of non-natural chiral β-aminoacid esters, a sub-class of chiral N-substituted allylic amines. Examples of chiral β-aminoacid esters that can be produced through the described method include, but are not limited to, N-(2-methylpent-1-en-3-yl)benzenamine and Ethyl 2-methylene-3-(phenylamino)butanoate). Further, chiral heterocycles, and bioactive molecules or materials can be produced from the products of the method disclosed herein. This method could be used in the pharmaceutical industry, the biotech industry, the agrochemical industry, the chemical industry, and the polymer industry, as well as any other industry where chiral amines are used.

Since many natural products, pharmaceutical compounds, and agrochemicals contain chiral amine functionality, the transition metal catalyzed asymmetric amination of olefins has received significant importance in organic synthesis. [You, S. et al., J. Am. Chem. Soc. 2001, 123, 7471; Hayashi, T. et al., Tetrahedron Lett. 1990, 31, 1743; Jorgensen, K. A. et al., Chem. Rev. 1998, 98, 1689; Evans, P. A. et al., J. Am. Chem. Soc. 1999, 121, 6761.] The direct and most efficient way to synthesize these chiral amines involves the direct functionalization of allylic C—H bonds via asymmetric allylic amination. Most efforts in asymmetric allylic amination use pre-functionalized allylic substrates, which require more synthetic steps than the method described herein. Additionally, prior methods utilize expensive Pd, Rh or Ir-based chiral complexes as the common catalysts [US 20060199728 A1] for asymmetric allylic amination of pre-functionalized allylic substrates. [Trost, B. M. et al. Chem. Pharm. Bull. 2002, 50, 1-14; Chem. Rev. 2003, 103, 2921-2943].

U.S. patent publication number US 2008/0194841 A1 and U.S. Pat. No. 6,399,787 B1 disclose the preparation of optically active β-aminoacids via asymmetric hydrogenation reaction. Alternate methods of producing chiral β-aminoacids and related chiral heterocycles mainly involve Aza Byalis-Hillman (ABH) reactions, which use N-protected imines and α,β-unsaturated carbonyl compounds. The major limitations of this ABH method include: i) the method is not useful for the preparation of chiral N-aryl allyl amines; and ii) the method's reaction rates are very poor. [Lamaty, F. et al., Chem. Rev. 2009, 109, 1-48].

US patent publication no. US 2008/0167312 A1 discloses the preparation of bioactive allyl amine Terbinafine and medical applications. US patent publication no. US 2006/0199728 A1 discloses Ir-based catalysts with phosphoramidite ligands for asymmetric allylic amination and etherification of allylic acetates.

The method described herein provides a simple and direct method for the production of chiral allyl amines by using simple olefins and inexpensive metal catalyst for asymmetric allylic amination, using a copper catalytic system.

In the method described herein, one reagent comprises an olefin containing allylic C—H group with the general structure R—C(C—HR$^1$)=CHR$^2$. The structure can be further represented as:

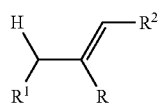

Useful olefins include, but are not limited to, the following examples:

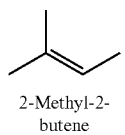

2-Methyl-2-butene

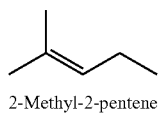

2-Methyl-2-pentene

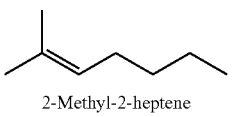

2-Methyl-2-heptene

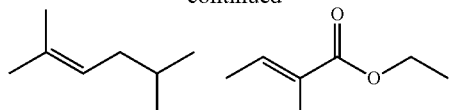

2,5-Dimethyl-2-hexene          Ethyltiglate

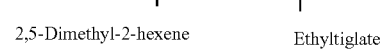

sec-Butyltiglate

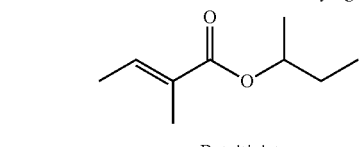

Benzyltiglate          methy-2-methyl-2-pentenoate

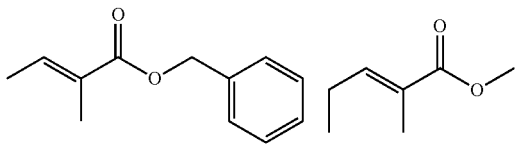

2-methyl-2-butenal     2-methyl-2-pentenal     3-methyl-3-penten-2-one

Combinations of above olefins may also be implemented in the method of invention.

In the method described herein, one reagent comprises an aminating reagent. The aminating reagents are substituted hydroxylamines Examples of aminating reagents which can be used include, but are not limited to, aryl hydroxylamines, N-Boc hydroxyl amines, Phenyl hydroxylamine, Tolyl hydroxylamine, 2-Iodophenyl hydroxylamine, and N-Boc hydroxylamine. The following aryl and N-Boc hydroxylamines are non-limiting examples of aminating reagents which may be used:

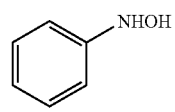

Phenyl Hydroxylamine

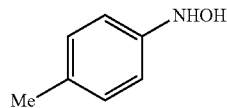

Tolyl Hydroxylamine

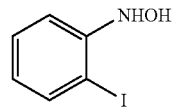

2-Iodophenyl Hydroxylamine

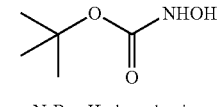

N-Boc Hydroxylamine

R(+)-BINAM may be used as the chiral ligand. The following chiral ligands are non-limiting examples of chiral ligands which may be utilized in the described method:

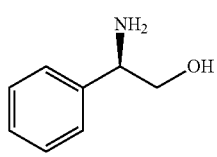

(6% ee)

R(+)-2-phenyl glycinol

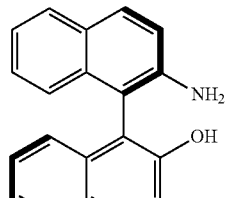

(28% ee)

R(+)-2'-amino-1,1'-Binapthalen-2-ol

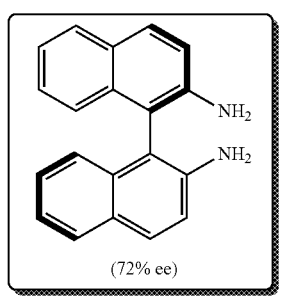

(72% ee)

R(+)-BINAM

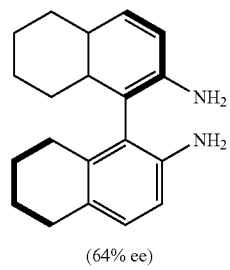

(64% ee)

Octahydro-R(+)-BINAM

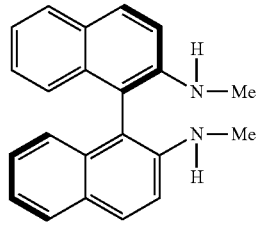

(23% ee)

R(+)-N, N'-dimethyl-binapthyldiamine

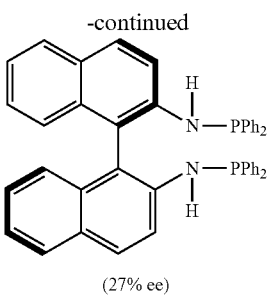

(27% ee)

R(+)-BINAM-P

Tetrakis(acetonitrile)copper(I) hexafluorophosphate, whose chemical formula is $[Cu(CH_3CN)_4]PF_6$, may be used as the copper (Cu(I)) compound.

Examples and Results

All experiments were performed under nitrogen atmosphere. Dichloromethane (dry, 99.99+) from Alfa Aesar was used as purchased. The following olefins were used in experiments: 2-methyl-2-pentene, 2-methyl-2-heptene, Ethyl tiglate, Methyl trans-2-methyl-2-pentenoate. All olefins, including tiglate esters, and N-Boc hydroxylamine were purchased from Sigma Aldrich and used as purchased. Most of the ligands and catalysts were purchased from Sigma-Aldrich and Strem chemicals, except octahydro R(+)-BINAM which was synthesized by the reduction of R(+)-BINAM ligand as described in Kano, T.; Tanaka, Y.; Osawa, K.; Yurino, T.; Maruoka, K. *J. Org. Chem.* 2008, 73, 7387. Arylhydroxylamines were synthesized by Zn-metal reduction of commercially available nitroarenes, as described in Kamm, O. *Org. Synth.* Col. Vol. I, 1958, p. 445.

IR spectra were recorded on JASCO 480-plus instrument. 1H and 13C NMR were recorded on Varian 400 MHz NMR using $CDCl_3$ solvent, unless otherwise noted. Products were confirmed by Agilent GC-MS (7890A-5975C). To measure enantiomeric excess, GC (HP Series II 5890) with chiral capillary column (Restek betadex-30 m×0.25×0.25μ) and HPLC (Dionex, Ultimate 3000) with Chiralpak AS-H column (4.6×250 mm 5μ) were used.

General Procedure for Asymmetric Allylic Amination:

Under nitrogen atmosphere, the solution of precatalyst copper (Cu(I)) compound $Cu(CH_3CN)_4PF_6$ (10 mg, 0.025 mmol) and ligand R(+)-BINAM (14 mg, 0.05 mmol) in dichloromethane (3 mL) was stirred at room temperature for ten (10) minutes. Then the olefin (1 mmol) was added followed by the slow addition of arylhydroxylamine (0.25 mmol) solution in dichloromethane (5 mL) via syringe pump over five (5) hours at room temperature. Reactions were allowed to continue for two (2) more hours to get complete consumption of arylhydroxylamine Once the product formation was confirmed by GC-MS, the mixture was filtered through celite and the filtrate was concentrated to dryness. The crude product was purified by column chromatography (Hexane/Ethylacetate eluents) to give the corresponding allyl amine product, which was then directly analyzed by NMR and chiral HPLC or chiral GC to determine the purity and enantiomeric excess.

Example 1

N-(2-methylpent-1-en-3-yl)benzenamine

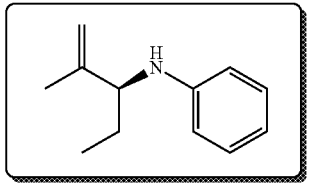

The solution of Cu(CH$_3$CN)$_4$PF$_6$ (10 mg, 0.025 mmol) and ligand R(+)-BINAM (14 mg, 0.05 mmol) in dichloromethane (3 mL) was stirred at room temperature for 10 minutes. To the same flask, addition of 2-methyl-2-pentene (1 mmol, 122 µL) was followed by the slow addition of phenylhydroxylamine (0.25 mmol, 27.5 mg) solution in dichloromethane (5 mL) via syringe pump over 5 hours at room temperature. Reaction was allowed to continue for two more hours to get complete consumption of phenylhydroxylamine. Product was confirmed by GC-MS (M$^+$=175.10) and NMR analysis. Pure allylamine obtained in 68% yield with an optical purity of 69% ee. Chiral GC: t$_r$=35.00 min (major), t$_r$=35.42 min (minor).

Example 2

N-(2-methylpent-1-en-3-yl)benzenamine

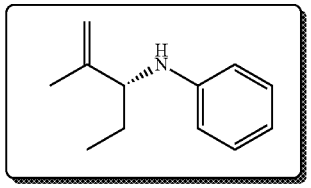

All the procedure is same as in Example 1, except that S(−)-BINAM was used in place of R(+)-BINAM. Pure allylamine obtained in 65% yield with an opposite enantioselectivity of 73% ee. Chiral GC: t$_r$=35.18 min (minor), t$_r$=35.58 min (major).

Example 3

N-(2-methylhept-1-en-3-yl)benzenamine

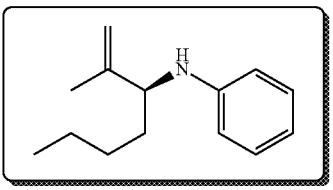

The solution of Cu(CH$_3$CN)$_4$PF$_6$ (10 mg, 0.025 mmol) and ligand R(+)-BINAM (14 mg, 0.05 mmol) in dichloromethane (3 mL) was stirred at room temperature for 10 minutes. To the same flask, addition of 2-methyl-2-heptene (1 mmol, 155 µL) was followed by the slow addition of N-phenylhydroxylamine (0.25 mmol, 27.5 mg) solution in dichloromethane (5 mL) via syringe pump over 5 hours at room temperature. Reaction was allowed to continue for two more hours to get complete consumption of N-phenylhydroxylamine. Product was confirmed by GC-MS (M$^+$=203.10) and NMR analysis. Pure allylamine obtained in 64% yield with an optical purity of 67% ee. Chiral GC: t$_r$=41.65 min (major), t$_r$=41.88 min (minor).

Example 4

4-methyl-N-(2-methylpent-1-en-3-yl)benzenamine

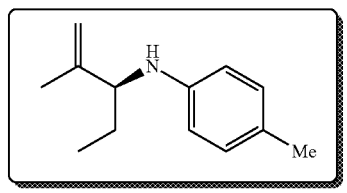

The solution of Cu(CH$_3$CN)$_4$PF$_6$ (10 mg, 0.025 mmol) and ligand R(+)-BINAM (14 mg, 0.05 mmol) in dichloromethane (3 mL) was stirred at room temperature for 10 minutes. To the same flask, addition of 2-methyl-2-pentene (1 mmol, 122 µL) was followed by the slow addition of N-tolylhydroxylamine (0.25 mmol, 31 mg) solution in dichloromethane (5 mL) via syringe pump over 5 hours at room temperature. Reaction was allowed to continue for two more hours to get complete consumption of N-tolylhydroxylamine Product was confirmed by GC-MS (M$^+$=189.10) and NMR analysis. Pure allylamine obtained in 62% yield with an optical purity of 74% ee. Chiral GC: t$_r$=38.56 min (major), t$_r$=39.07 min (minor).

Example 5

4-methyl-N-(2-methylhept-1-en-3-yl)benzenamine

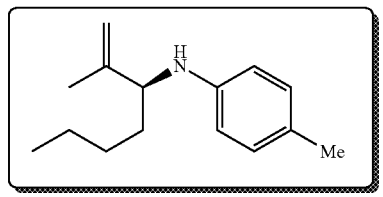

The solution of Cu(CH$_3$CN)$_4$PF$_6$ (10 mg, 0.025 mmol) and ligand R(+)-BINAM (14 mg, 0.05 mmol) in dichloromethane (3 mL) was stirred at room temperature for 10 minutes. To the same flask, addition of 2-methyl-2-heptene (1 mmol, 155 µL) was followed by the slow addition of N-tolylhydroxylamine (0.25 mmol, 31 mg) solution in dichloromethane (5 mL) via syringe pump over 5 hours at room temperature. Reaction was allowed to continue for two more hours to get complete consumption of N-tolylhydroxylamine Product was confirmed by GC-MS (M$^+$=217.20) and NMR analysis. Pure allylamine obtained in 59% yield with an optical purity of 66% ee. Chiral GC: t$_r$=44.98 min (major), t$_r$=45.28 min (minor).

Example 6

Ethyl 2-methylene-3-(phenylamino)butanoate

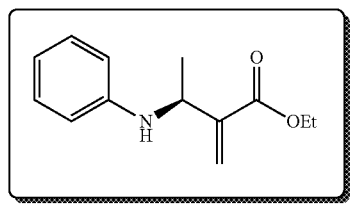

The solution of Cu(CH$_3$CN)$_4$PF$_6$ (10 mg, 0.025 mmol) and ligand R(+)-BINAM (14 mg, 0.05 mmol) in dichloromethane (3 mL) was stirred at room temperature for 10 minutes. To the same flask, addition of Ethyltiglate (0.75 mmol, 104 μL) was followed by the slow addition of N-phenylhydroxylamine (0.25 mmol, 27.5 mg) solution in dichloromethane (5 mL) via syringe pump over 5 hours at room temperature. Reaction was allowed to continue for two more hours to get complete consumption of N-phenylhydroxylamine. Product was confirmed by GC-MS (M$^+$=219.00) and NMR analysis. Pure allylamine obtained in 78% yield with an optical purity of 42% ee. Chiral HPLC: Chiralpak AS-H column using Hexanes/Ethanol/DEA (99:1:0.02) as mobilephase with a flow rate of 0.30 mL/min; t$_r$=17.367 min (major), t$_r$=18.417 min (minor).

Example 7

Ethyl 3-(p-tolylamino)-2-methylenebutanoate

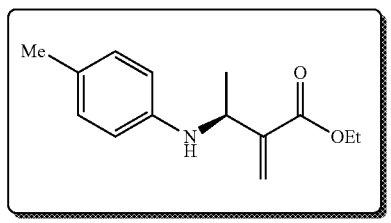

The solution of Cu(CH$_3$CN)$_4$PF$_6$ (10 mg, 0.025 mmol) and ligand R(+)-BINAM (14 mg, 0.05 mmol) in dichloromethane (3 mL) was stirred at room temperature for 10 minutes. To the same flask, addition of Ethyltiglate (0.75 mmol, 104 μL) was followed by the slow addition of N-tolylhydroxylamine (0.25 mmol, 27.5 mg) solution in dichloromethane (5 mL) via syringe pump over 5 hours at room temperature. Reaction was allowed to continue for two more hours to get complete consumption of N-tolylhydroxylamine. Product was confirmed by GC-MS (M$^+$=232.90) and NMR analysis. Pure allylamine obtained in 69% yield with an optical purity of 34% ee. Chiral HPLC: Chiralpak AS-H column using Hexanes/Ethanol/DEA (99:1:0.02) as mobile phase with a flow rate of 0.35 mL/min; t$_r$=14.108 min (minor), t$_r$=15.467 min (major).

Example 8

Methyl 2-methylene-3-(phenylamino)pentanoate

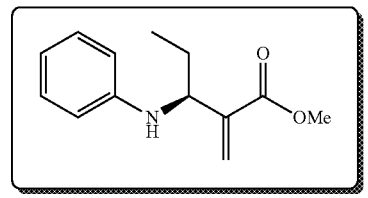

The solution of Cu(CH$_3$CN)$_4$PF$_6$ (10 mg, 0.025 mmol) and ligand R(+)-BINAM (14 mg, 0.05 mmol) in dichloromethane (3 mL) was stirred at room temperature for 10 minutes. To the same flask, addition of Methyl trans-2-methyl-2-pentenoate (0.75 mmol, 105 μL) was followed by the slow addition of N-phenylhydroxylamine (0.25 mmol, 27.5 mg) solution in dichloromethane (5 mL) via syringe pump over 5 hours at room temperature. Reaction was allowed to continue for two more hours to get complete consumption of N-phenylhydroxylamine. Product was confirmed by GC-MS (M$^+$=219.10) and NMR analysis. Pure allylamine obtained in 73% yield with an optical purity of 33% ee. Chiral separation with NMR using shift reagent (CDCl$_3$): δ 4.80 (major), δ 4.83 (minor).

New Matter

Figure 2:
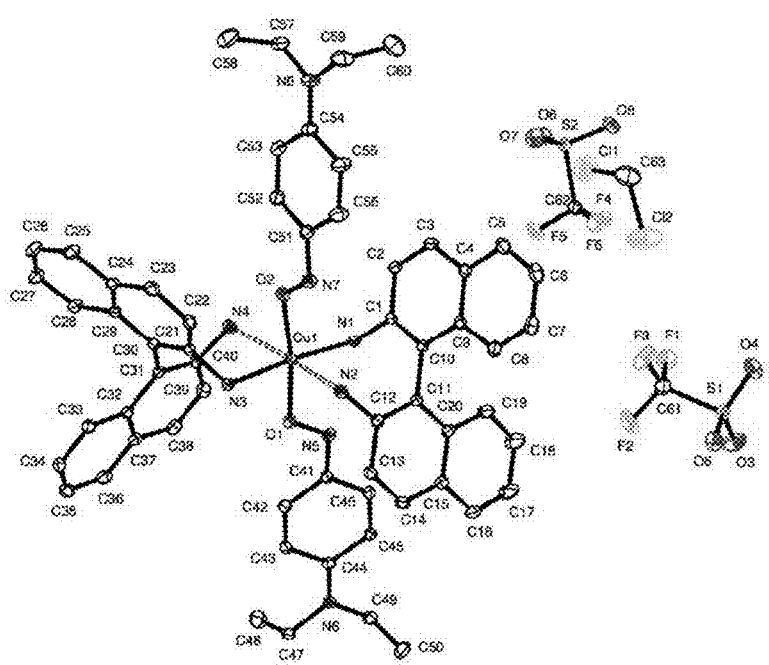
FIG. 2 is an X-Ray structure of the Cu-BINAM-nitroso complex.

A novel catalytic intermediate has been synthesized and isolated that is relevant to the asymmetric allylic amination procedure. This novel catalytic intermediate, which comprises a chiral Cu-complex. It is a chiral copper-BINAM nitrosoarene complex [Cu(BINAM)$_2$(ArNO)$_2$]OTf$_2$. OTf is a triflate functional group as would be recognized by one having skill in the art. X-Ray crystallographic analysis of [Cu(BINAM)2(ArNO)2]OTf2 confirms the coordination of two BINAM ligands and two notrosoarenes (ArNO) to the Cu-metal. An ORTEP view of the X-Ray structure with atomic numbering scheme of the Cu-BINAM-nitroso complex is set forth as FIG. 2. The previously reported and understood Cu-complexes exhibits coordination through the nitrogen atom. However, the present composition of matter does not share this common coordination; instead this novel Cu-complex indicates the coordination of nitrosoarene through the Oxygen atom (O→Cu). This exhibits a staunch difference in the reactivity likely due to the change in electron density at the metal center resulting from the BINAM ligands attached to it.

Structurally, the present complex is similar to copper-superoxo complexes that generally exist as copper-monooxygenase enzymes. Yet, they are molecularly distinct. Most metal-nitroso complexes involve in coordination through the nitrogen-atom, instead of oxygen. However, the fact X-Ray crystallographic analysis has confirmed that the nitrosoarene moiety of [Cu(BINAM)2(ArNO)2]OTf2 is coordinated through its oxygen atom is substantial. The catalytic implications of this metal complex will assist in the understanding of reaction mechanisms and selectivity, particularly in the asymmetric allylic amination procedure. Therefore, in addition to its clear uses in academic research, the complex has a direct use in both chemical and pharmaceutical industries such as for the design and development of novel catalytic reactions. Likewise, because of the existing structural similarities, the current structure can also be useful in predicting mechanistic pathways of copper-monooxygenase enzymes in biological systems.

An embodiment of a scheme for the synthesis [Cu(BINAM)2(ArNO)2]OTf2 is provided below. A mixture of [Cu(OTf)$_2$] (0.635 g, 1.76 mmol) and R(+)-BINAM ligand (1.0 g, 3.52 mmol) was created. To this mixture, 10 mL toluene was added. The mixture was stirred at room temperature for 6 hours, after which the solvent was removed under vacuum and the crude product which was directly re-crystallized from ethylacetate:hexane mixture (5:1) to obtain pure [Cu(BINAM)2]OTf2 complex (1.28 g, 78% yield).

In order to obtain crystals suitable for X-ray diffraction, the Cu-complex (1.28 g, 1.37 mmol) obtained above was dissolved in dichloromethane (10 mL) and N,N-diethyl-4-nitrosoaniline (0.40 g, 2.2 mmol) was added. It is immediately noted that the dark brown solution becomes dark green. After stirring overnight (15 h), the dark green solution was filtered, and the solvent was removed on rotavap. The solid residue was triturated with diethyl ether (10 mL×2). Recrystallization from CH2Cl2/haxane at −20° C. provided dark greenish crystals suitable for X-ray diffraction.

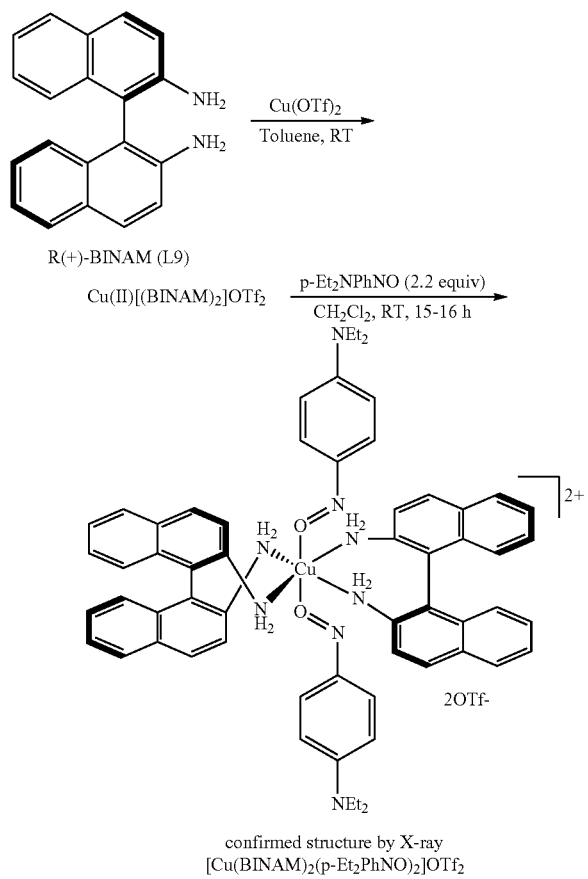

confirmed structure by X-ray
[Cu(BINAM)2(p-Et2PhNO)2]OTf2

For the purpose of understanding the original method of producing the composition of matter described herein, references are made in the text to exemplary embodiments of a method of producing or synthesizing the matter of composition, only some of which are described herein. It should be understood that no limitations on the scope of the invention are intended by describing these exemplary methods. One of ordinary skill in the art will readily appreciate that alternate but functionally equivalent components, materials, designs, and equipment may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

Reference throughout this specification to features, advantages, or similar language does not imply that all of the features and advantages that may be realized should be or are in any single embodiment. Rather, language referring to the features and advantages is understood to mean that a specific feature, advantage, or characteristic described in connection with an embodiment is included in at least one embodiment. Thus, discussion of the features and advantages, and similar language, throughout this specification may, but do not necessarily, refer to the same embodiment.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment.

Moreover, the terms "substantially" or "approximately" as used herein may be applied to modify any quantitative representation that could permissibly vary without resulting in a change to the basic function to which it is related.

All references to patents, documents, and other writings are incorporated by reference and their inclusion herein shall not be construed as an admission as to their status with respect to being or not being prior art.

The invention claimed is:

1. A chemical compound having the formula [Cu(BINAM)$_2$(ArNO)$_2$]OTf$_2$.

2. The chemical compound of claim 1 wherein the compound is a chiral copper-BINAM nitrosoarene complex.

3. A chemical compound comprising:
   a. a copper atom;
   b. two nitrosoarenes;
   c. two BINAM ligands;
   d. two triflates.

4. The chemical compound of claim 3 wherein the compound is a chiral copper-BINAM-nitrosoarene complex.

5. The chemical compound of claim 3 wherein the copper-nitroso complex is chiral.

6. The chemical compound of claim 3 wherein at least one ligand is chiral.

7. The chemical compound synthesized from the process of combining copper triflate (Cu(OTf)$_2$), and R(+)-BINAM in the presence of toluene.

8. The chemical compound of claim 7 wherein the process comprises the steps of first creating a mixture of Cu(OTf)$_2$, R(+)-BINAM, and toluene, stirring the mixture, and removing the solvent once a desired chemical compound is produced.

* * * * *